(12) United States Patent
Rees et al.

(10) Patent No.: US 6,812,196 B2
(45) Date of Patent: Nov. 2, 2004

(54) BIOCIDAL CLEANER COMPOSITION CONTAINING ACID-ANIONIC SURFACTANT-ALCOHOL COMBINATIONS AND METHOD OF USING THE COMPOSITION

(75) Inventors: Wayne M. Rees, Racine, WI (US); Debra S. Hilgers, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 107 days.

(21) Appl. No.: 10/166,510

(22) Filed: Jun. 10, 2002

(65) Prior Publication Data

US 2003/0083219 A1 May 1, 2003

Related U.S. Application Data

(63) Continuation-in-part of application No. 09/587,453, filed on Jun. 5, 2000, now abandoned.

(51) Int. Cl.$^7$ ................................................ C11D 17/00
(52) U.S. Cl. ........................ 510/238; 510/239; 510/382; 510/402; 510/426; 510/488; 510/506; 134/40; 134/41; 134/42
(58) Field of Search ............................... 510/238, 239, 510/403, 426, 488, 506, 382; 134/40, 41, 42

(56) References Cited

U.S. PATENT DOCUMENTS

| | | |
|---|---|---|
| 3,141,821 A | 7/1964 | Compeau |
| 3,591,510 A | 7/1971 | Zenk |
| 3,652,420 A | 3/1972 | Hill |
| 3,969,258 A | 7/1976 | Carandang et al. |
| 4,086,178 A | 4/1978 | Walker |
| 4,321,156 A | 3/1982 | Bushman |
| 4,404,040 A | 9/1983 | Wang |
| 4,465,612 A | 8/1984 | Altenschopfer et al. |
| 4,606,842 A | 8/1986 | Keyes et al. |
| 4,612,137 A | 9/1986 | Kuroda et al. |
| 4,647,458 A | 3/1987 | Ueno et al. |
| 4,678,658 A | 7/1987 | Casey et al. |
| 4,715,980 A | 12/1987 | Lopes et al. |
| 4,734,222 A | 3/1988 | Winterton et al. |
| 4,749,509 A | 6/1988 | Kacher |
| 4,753,748 A | 6/1988 | Laitem et al. |
| 4,759,867 A | 7/1988 | Choy et al. |
| 4,767,558 A | 8/1988 | Ouhadi et al. |
| 4,806,173 A | 2/1989 | Toukan |
| 4,812,252 A | 3/1989 | Nambudiry |
| 4,863,629 A | 9/1989 | Osberghaus et al. |
| 4,954,283 A | 9/1990 | Schmid et al. |
| 4,965,009 A | 10/1990 | Baur et al. |
| 4,965,013 A | 10/1990 | Pratt |
| 4,966,724 A | 10/1990 | Culshaw et al. |
| 4,983,317 A | 1/1991 | Requejo et al. |
| 5,008,030 A | 4/1991 | Cook et al. |
| 5,039,441 A | 8/1991 | Thomas et al. |
| 5,234,719 A | 8/1993 | Richter et al. |
| 5,254,336 A | 10/1993 | Hoshowski et al. |
| 5,320,772 A | 6/1994 | Tricca |
| 5,324,443 A | 6/1994 | Arif et al. |
| 5,328,633 A | 7/1994 | Hasting et al. |
| 5,389,283 A | 2/1995 | Held, III |
| 5,411,598 A | 5/1995 | Tsao et al. |
| 5,411,666 A | 5/1995 | Hollis et al. |
| 5,415,814 A | 5/1995 | Ofosu-Asante et al. |
| 5,441,723 A | 8/1995 | Simmons |
| 5,512,186 A | 4/1996 | Wright et al. |
| 5,531,939 A | 7/1996 | Haley et al. |
| 5,585,340 A | 12/1996 | Held, III |
| 5,599,785 A | 2/1997 | Mondin et al. |
| 5,602,093 A | 2/1997 | Haerer et al. |
| 5,607,597 A | 3/1997 | Wright et al. |
| 5,670,055 A | 9/1997 | Yu et al. |
| 5,731,275 A | 3/1998 | Prevost et al. |
| 5,744,439 A | 4/1998 | Bonett |
| 5,749,924 A | 5/1998 | Murch et al. |
| 5,750,198 A | 5/1998 | Furuyama et al. |
| 5,780,416 A | 7/1998 | Kiewert et al. |
| 5,851,980 A | 12/1998 | Avery |
| 5,872,088 A | 2/1999 | Pucci et al. |

(List continued on next page.)

FOREIGN PATENT DOCUMENTS

| | | |
|---|---|---|
| WO | WO 96/33951 | 10/1996 |
| WO | WO 97/15649 | 5/1997 |
| WO | WO 00/32737 | 6/2000 |
| WO | WO 01/00777 | 1/2001 |

OTHER PUBLICATIONS

J. Costerton, et al., "Microbial Biofilms," Ann. Rev. Microbiol. 49:711–745, 1995.

J. Costerton, "Overview of Microbial Biofilms," J. Indust. Microbiol. 15:137–140, 1995.

J. Costerton and P. Stewart, "Battling Biofilms," Scient. Am. pp. 75–81, 2001.

E. De Lancy Pulcini, "Bacterial Biofilms: A Review of Current Research," Nephrologie 22(8):439–441, 2001.

P. Gilbert, et al., "Assessment of Resistance Towards Biocides Following the Attachment of Micro–organisms to, and Growth on, Surfaces," J. App. Microbiol. 91:248–254 2001.

X. Liu, et al., "Resistance of Biofilmsto the Catalase Inhibitor 3–Amino–1,2,4–triazole," Biotechnol. Bioengineer. 59(2):156–162, 1998.

P.S. Stewart, et al., "Biofilm Penetration and Disinfection Efficacy of Alkaline Hypochlorite and Chlorosulfamates," J. App. Microbiol. 91:525–532, 2001.

*Primary Examiner*—Necholus Ogden

(57) ABSTRACT

A method of substantially reducing biofilm-associated microorganisms on a surface and a composition designed to substantially reduce biofilm-associated microorganisms on surfaces are disclosed. In one embodiment, the composition is an anionic surfactant selected from the group consisting of alkyl sulfates, alkyl sulfonates, and aryl sulfonates with alkyl or aryl substituents, an acid, and an alcohol solvent, wherein the pH of the composition is between pH 1 and pH 5.

21 Claims, No Drawings

U.S. PATENT DOCUMENTS

| | | |
|---|---|---|
| 5,891,392 A | 4/1999 | Monticello et al. |
| 5,908,856 A | 6/1999 | Oldenhove |
| 5,910,420 A | 6/1999 | Tuompo et al. |
| 5,910,475 A | 6/1999 | Neumiller et al. |
| 5,929,016 A | 7/1999 | Harrison |
| 5,942,480 A | 8/1999 | Prevost et al. |
| 5,958,852 A | 9/1999 | Yianakopoulos et al. |
| 5,962,388 A | 10/1999 | Sherry et al. |
| 5,977,041 A | 11/1999 | Honda |
| 6,004,438 A | 12/1999 | Woodson |
| 6,027,572 A | 2/2000 | Labib et al. |
| 6,030,936 A | 2/2000 | Lu et al. |
| 6,039,965 A | 3/2000 | Donlan et al. |
| 6,046,148 A | 4/2000 | Toussaint et al. |
| 6,090,771 A | 7/2000 | Burt et al. |
| 6,096,225 A | 8/2000 | Yang et al. |
| 6,106,774 A | 8/2000 | Monticello et al. |
| 6,110,295 A | 8/2000 | Lu et al. |
| 6,136,770 A | 10/2000 | Cheung et al. |
| 6,140,284 A | 10/2000 | Cheung et al. |
| 6,143,703 A | 11/2000 | Cheung et al. |
| 6,143,710 A | 11/2000 | Lu et al. |
| 6,150,318 A | 11/2000 | Silvester et al. |
| 6,159,924 A | 12/2000 | Weller et al. |
| 6,177,388 B1 | 1/2001 | Cheung et al. |
| 6,184,195 B1 | 2/2001 | Cheung et al. |
| 6,197,315 B1 | 3/2001 | Beerse et al. |
| 6,197,738 B1 | 3/2001 | Regutti |
| 6,204,230 B1 | 3/2001 | Taylor et al. |
| 6,221,823 B1 | 4/2001 | Crisanti et al. |
| 6,221,833 B1 | 4/2001 | Colurciello, Jr. |
| 6,239,092 B1 | 5/2001 | Papasso et al. |
| 6,251,844 B1 | 6/2001 | Leonard et al. |
| 6,255,269 B1 | 7/2001 | Leonard et al. |
| 6,265,366 B1 | 7/2001 | Bonett |
| 6,302,969 B2 | 10/2001 | Moster et al. |

BIOCIDAL CLEANER COMPOSITION CONTAINING ACID-ANIONIC SURFACTANT-ALCOHOL COMBINATIONS AND METHOD OF USING THE COMPOSITION

CROSS-REFERENCE TO RELATED APPLICATION

This application is a continuation-in-part of U.S. Ser. No. 09/587,453, filed Jun. 5, 2000 now abandoned.

STATEMENT REGARDING FEDERALLY SPONSORED RESEARCH OR DEVELOPMENT

Background of the Invention

Eliminating pathogenic microorganisms on various hard or soft surfaces typically found in residential homes and institutional environments, especially is where such organisms may stay active for relatively long periods of time, is critical to good cleaning and hygiene practices (S. F. Bloomfield and E. Scott, *J. Appl. Microbiol.* 83:1–9, 1997). Exemplary hard surfaces include counter-tops, bath tubs, sinks, drains, shower stalls and toilet bowls. Soft surfaces can be woven or nonwoven textiles such as shower curtain liners, clothing, carpeting and upholstery. There is a growing scientific recognition that bacterial organisms which actively populate these common surfaces may form organized communities called biofilms. Bacterial cells forming these biofilm communities assume a biological phenotype that is markedly different than their corresponding planktonic (non-surface attached) bacterial analogs (W. G. Characklis, "Microbial Biofouling Control" in *Biofilms*, Characklis and Marshall, eds., Wiley & Sons, 1990, J. W. Costerton, *Ann. Rev. Microb.* 49:7110–7145,1995). For example, current antimicrobial test methods for household cleaners employ a microbial inoculum of living planktonic bacteria.

One differentiating property between biofilm and planktonic bacteria is the greatly enhanced resistance to antimicrobial agents displayed by biofilm organisms. The significantly decreased susceptibility of biofilm cells to biocides has been documented in numerous recent studies. See for example: A. B. Ronner, et al., *J. Food Prot.* 56:750–758, 1993; J. W. Costerton, supra, 1995, P. Gilbert and M. R. W. Brown, *Microbial Biofilms*, Lappin-Scott and Costerton, Eds., University Press, 1995; S. Oie, et al., *Microbios.* 85:223–230, 1996; J. R. Das, et al., *Changes In Biocide Susceptibility of Bacteria Following Attachment to Surfaces*, poster presentation, American Society of Microbiology Conference on Microbial Biofilms, Snowbird, Utah, 1997; C. Ntasama-Essomba, et al., *Veter. Res.* 28:353–363, 1997, J. W. Costerton, *Internat. J. Antimicrob. Agents* 11:217–221, 1999.

This enhanced resistance to biocides for biofilm bacteria has been documented for antimicrobial agents traditionally used in biocidal cleaners for the residential home and institutional environments, such as quaternary ammonium compounds and chlorine-based oxidizing agents. Sanitizing and disinfecting cleaners using biocidal actives such as these may not meet required levels of microbial kill when used according to label instructions to treat biofilm-containing soils.

Effective cleaning of biofilm contaminated surfaces in residential homes and commercial institutions is essential for the maintenance of good environmental hygiene, where soils attached to surfaces are likely to contain biofilms (S. F. Bloomfield and E. Scott, supra, 1997). Thus, there is a significant need for biocidal compositions, which display high sanitizing and disinfecting power against biofilm-based microorganisms. Such compositions should be "user-friendly", presenting minimal chemical hazard to the user. In addition, these cleaners should perform effectively under practical use conditions, such as short contact times and room temperature application. Ideally, such compositions would also be inexpensive, i.e., they would be largely aqueous in nature and utilize low cost reagents.

Specific biocidal compositions and/or methods for their use, which specifically address biocide resistant forms of bacteria, have been disclosed. For example, U.S. Pat. Nos. 5,444,094 and 5,908,854 disclose biocidal compositions and related methods of use involving combinations of select solvents with quaternary ammonium compounds for biocidal cleaners effective against mycobacteria, such as *M. tuberculosis*. U.S. Pat. No. 5,731,275 discloses aqueous cleaning and decontaminating compositions for use on biofilm coated surfaces. However, the cleaning and disinfecting conditions cited in U.S. Pat. No. 5,731,275 involve soaking the biofilm-contaminated surfaces in the inventive cleaning solutions for extended periods of time, typically 12–24 hours at room temperature. Such treatment conditions are unrealistic for most residential home and institutional cleaning applications where the user typically applies the biocidal product to the contaminated surface by spraying, followed by a short contact time (usually 10 minutes or less).

BRIEF SUMMARY OF THE INVENTION

The present invention provides biocidal compositions that are highly effective at killing gram negative and gram positive biofilm-bound microorganisms and also address one or more of the above-mentioned technical formulation issues.

The present invention also provides a method for the effective sanitizing or disinfecting of biofilm-contaminated surfaces, comprising the steps of contacting or treating said surface with the described compositions of this invention.

In one embodiment, the present invention is a method of substantially reducing biofilm microorganisms on a surface comprising the step of applying a composition comprising (a) between 0.1% and 10% by weight of an anionic surfactant selected from the group consisting of alkyl sulfates, alkyl sulfonates, and aryl sulfonates with alkyl or aryl substituents; (b) between 0.1% and 10% by weight of an acid, preferably a weakly acidic organocarboxylic acid; and (c) between 0.5% and 10% by weight of a monohydric alcohol solvent. The pH of the composition is between pH 1 and pH 5, preferably between pH 2 and pH 4.

In a preferred version of the present invention, the anionic surfactant is present in an amount from about 0.25 to 8% by weight of the composition and is selected from the group consisting of sodium lauryl sulfate or sodium dodecylbenzene sulfonate.

In another preferred embodiment of the present invention, the acid is present in an amount between about 0.5% to about 5% by weight of the composition and is selected from the group consisting of citric acid, lactic acid, glycolic acid, gluconic acid, glucoheptonic acid, malic acid, glutaric acid, succinic acid, adipic acid, formic acid, oxalic acid, acetic acid, propanoic acid, benzoic acid, phthalic acid, malonic acid, sorbic acid, fumaric acid, tartaric acid, and mixtures thereof.

In another preferred embodiment of the present invention, the solvent is present in an amount of about 1.0% to about 5% by weight of the composition and is selected from the group consisting of aliphatic alcohols or a glycol ether.

The present invention is also a composition comprising (a) between 0.1% and 10% by weight of an anionic surfactant selected from the group consisting of alkyl sulfates, alkyl sulfonates, and aryl sulfonates with alkyl or aryl substituents, (b) between 0.1% and 10% by weight of an acid, and (c) between 0.5% and 10% of an aliphatic alcohol or glycol ether solvent, wherein the pH of the composition is between pH 1 and pH 5.

Other objects, advantages and features of the present invention are apparent to one of skill in the art after review of the specification and claims.

DETAILED DESCRIPTION OF THE INVENTION

We have discovered that the use of particular anionic surfactants in combination with an effective amount of select acids and specific alcohol or glycol ether solvents provides a composition with strong biocidal properties that is substantially reduce the number of microorganisms in biofilms. By "biofilms" we mean to include any of the systems described above in the Background section as biofilms and to also include systems described by similar terms such as "slime layer" and "biofouling."

This invention is directed to a method of cleaning and substantially reducing the biofilm microorganism contamination present on a substrate by the application of the antimicrobial solution of the present invention to the substrate by wiping, mopping, spraying, misting, dripping, or the like. (By "substantial reduction" we mean that the number of both gram positive and gram negative biofilm microorganisms are reduced by a log reduction of at least 4.0, preferably $\geq 4.5$, more preferably $\geq 5.0$ and most preferably at least $\geq 6.0$, at a contact time of 5 minutes or less compared to controls, as described below.) In another embodiment of the present invention, the reduction takes place at a contact time of 1 minute or less. The method may comprise a single step of applying the solution onto the substrate without direct physical removal or may comprise both application and removal steps such as spraying followed by wiping with a cloth.

More particularly, this invention is directed to an antimicrobial composition comprising greater than 0.1% by weight of at least one anionic surfactant selected from the group of alkyl sulfates, alkyl sulfonates and aryl sulfonates with alkyl or aryl substituents. Preferably, the amount of anionic surfactant is between 0.1% and 10%. Most preferably, the amount of anionic surfactant is between 0.5% and 5%.

Preferred examples of surfactants include alkali metal or ammonium salts of n-alkyl sulfates, n-alkyl sulfonates; and aryl sulfonates with alkyl or aryl substituents.

Preferably, the surfactant is selected from the group consisting of:

(i) linear $C_8$ to $C_{16}$ alkyl sulfates;
(ii) linear $C_8$ to $C_{16}$ alkyl sulfonates;
(iii) $C_8$ to $C_{16}$ alkyl benzenesulfonates;
(iv) $C_6$ to $C_{16}$ alkyl diphenyloxide disulfonates; and
(v) $C_4$ to $C_{16}$ alkylated naphthalene sulfonates.

The anionic surfactant is most preferably an n-alkyl sulfate such as sodium lauryl sulfate (hereinafter "SLS"), an alkyl benzene sulfonate such as sodium dodecyl benzene sulfonate (hereinafter "SDBS"), or mixtures thereof. Other exemplary anionic surfactants include dodecyldiphenyloxide disulfonate such as those sold under the tradename Dowfax 2A1® from The Dow Chemical Company, or sodium n-octylsulfonate such as Bioterge PAS-8® from the Stepan Company.

Most preferably, the anionic surfactant is selected from those utilizing an alkali metal or ammonium cation, due to their relatively low cost. The most preferable alkali metal is sodium because of the widespread commercial availability and low cost of the sodium salts of these anionic surfactants.

The surfactant is combined with an effective amount of at least one acid to provide the composition with a pH between 1–5, preferably 2–4. The acid is selected from the group consisting of weak acids having a dissociation constant of about $1 \times 10^{-2}$ to about $1 \times 10^{-5}$ in water at 25° C.

Exemplary acids of the present invention include citric acid, lactic acid, glycolic acid, gluconic acid, glucoheptonic acid, malic acid, malonic acid, glutaric acid, succinic acid, adipic acid, formic acid, oxalic acid, acetic acid, propanoic acid, benzoic acid, phthalic acid, and mixtures thereof. Other suitable acids are polymeric organocarboxylic acids such as low molecular weight (molecular weight, average, $M_w$, below about 50,000) poly(acrylic acid) and poly(maleic) acid homopolymers and copolymers such as Goodrite K-7058® available from BF Goodrich Speciality Chemicals and Belclene 901@ available from FMC Corporation.

Other acids such as organo-phosphonic, and organo-sulfonic acids, and mineral acids are also acceptable. The main criteria here is that the pH of the antimicrobial composition (as used) is less than about 5, and ideally below about 4. The acid should be present at concentrations >0.1%. The preferred range is about 0.25 to 8% by weight in the composition. The most preferred range is about 0.5 to 5% by weight in the composition.

To minimize possible corrosion problems on certain household surfaces and potential safety issues associated with skin contact in acidic conditions, a pH in the range of between about 2 to 4 range is preferred. It is also believed that this pH range provides some cleaning efficacy against low to moderate levels of hard-water (mineral soil) stains.

To the combination of surfactant and acid, one would add at least one monohydric aliphatic alcohol or glycol ether solvent. Ideally the composition contains at least one alcohol or glycol ether, which is only sparingly soluble in water (soluble at less than 20% by weight in water) such as benzyl alcohol, n-butyl alcohol, ethylene glycol n-hexyl ether or propylene glycol n-butyl ether. The solvent(s) should be present at concentrations of about 0.5% or greater (in total). The preferred solvent concentration range is about 0.5–10% by weight in the composition. These solvents are employed to enhance the cleaning and antimicrobial properties of the compositions.

Exemplary solvents include those selected from the following formulae:

(I) R—O—$CH_2CH_2$—OH, where R is butyl, pentyl, hexyl, phenyl, or benzyl;

(II) R—O—$(CH_2CH_2\text{-}0)_2$H, where R is butyl, pentyl, hexyl, phenyl, or benzyl;

(III) R'—O—$CH_2CH$—$(CH_3)$OH, where R' is propyl, butyl, pentyl, hexyl, phenyl, or benzyl;

(IV) R'—$O(CH_2CH$—$(CH_3)O)_2$H, where R' is methyl, ethyl, propyl, butyl, pentyl, hexyl, phenyl, or benzyl;

(V) R"—OH, where R" is $C_nH_{2n+1}$, where $n \geq 4$, and (VI) R'"—OH, where R'"=benzyl, $C_6H_5$—$CH_2CH_2$ Exemplary glycol ethers include ethylene glycol monobutyl ether, available under the tradename Butyl Cellosolve® from Union Carbide Corp.; ethylene glycol monohexyl ether, available under the tradename Hexyl Cellosolve® from Union Carbide Corp., and ethylene glycol phenyl ether, available under the tradename Dowanol EPh® from The Dow Chemical Company.

The solution may be combined by methods known to those of skill in the art. The solution can be aqueous or non-aqueous. Aqueous solutions are most preferred. The aqueous solution of this invention will generally contain an amount of water in the range from about 50 to about 99% w/w, and preferably, from about 85 to about 98% w/w.

Other additives known in the cleaning and disinfecting arts may be included in the inventive solution. Such additives include, for example, viscosity enhancing agents, colorants, fragrances, preservatives and stabilizers.

EXAMPLES

A. Acid-Anionic Cleaning Compositions that Provide Biocidal Efficacy against Biofilm Organisms Test Formulations

TABLE 1

Acidic Formulations

| Reagents | 1 | 2 | 3 | 4 | 5 | 6 | 7 |
|---|---|---|---|---|---|---|---|
| Lactic Acid | 0.50% | 0.50% | 0.50% | 0.50% | 0.50% | 0.50% | — |
| Glycolic Acid | — | — | — | — | — | — | — |
| Citric Acid | — | — | — | — | — | — | 0.50% |
| Diethylene Glycol Ethyl Ether | — | 2.00% | 2.00% | 2.00% | — | 2.00% | 2.00% |
| Ethylene Glycol n-Hexyl Ether | — | 0.75% | 1.50% | 1.00% | — | 1.50% | 1.00% |
| Isopropanol | — | — | — | — | 3.00% | — | — |
| Sodium Lauryl Sulfate | — | — | — | 0.50% | — | — | 0.50% |
| Sodium Dodecyl Benzene Sulfonate | 0.50% | — | 0.50% | — | 0.50% | — | — |
| Sodium n-Octyl Sulfate | — | — | — | — | — | 0.50% | — |
| pH | 2.6 | 2.1 | 2.5 | 2.5 | 2.6 | 2.6 | 2.5 |

| Reagents | 8 | 9 | 10 | 11 | 12 | 13 | 14 |
|---|---|---|---|---|---|---|---|
| Lactic Acid | — | 0.50% | 0.50% | 0.50% | 0.50% | 0.50% | 0.50% |
| Glycolic Acid | 0.50% | — | — | — | — | — | — |
| Diethylene Glycol Ethyl Ether | 2.00% | 2.00% | — | 4.00% | — | 2.00% | 2.00% |
| Ethylene Glycol n-Hexyl Ether | 1.50% | — | — | — | 2.00% | — | — |
| Isopropanol | — | — | — | — | — | — | — |
| Sodium Dodecyl Benzene Sulfonate | 0.50% | 0.50% | 0.50% | 0.50% | 0.50% | 0.50% | 0.50% |
| Ethylene Glycol Mono-Pentyl Ether | — | 1.90% | — | — | — | — | — |
| n-Butanol | — | — | 5.00% | — | — | — | — |
| Ethylene Glycol n-Phenyl Ether | — | — | — | — | 2.00% | 2.00% | — |
| Benzyl Alcohol | — | — | — | — | — | — | 3.00% |
| pH | 2.5 | 2.5 | 2.5 | 2.5 | 2.6 | 2.6 | 2.5 |

TABLE 2

Neutral Formulations

| Reagents | 15 | 16 | 17 |
|---|---|---|---|
| Sodium Lactate | 0.50% | — | — |
| Sodium Glycolate | — | 0.50% | — |
| Trisodium Citrate | — | — | 0.50% |
| Diethylene Glycol Ethyl Ether | 2.00% | 2.00% | 2.00% |
| Ethylene Glycol n-Hexyl Ether | 1.00% | 1.00% | 1.00% |
| Sodium Dodecyl Benzene Sulfonate | 0.60% | 0.60% | 0.60% |
| pH | 6.5 | 6.5 | 6.5 |

TABLE 3

Alkaline Formulations

| Reagents | 18 | 19 |
|---|---|---|
| Sodium Lactate | 0.50% | — |
| Sodium Glycolate | — | 0.50% |
| Diethylene Glycol Ethyl Ether | 2.00% | 2.00% |
| Ethylene Glycol n-Hexyl Ether | 1.00% | 1.00% |
| Sodium Dodecyl Benzene Sulfonate | 0.60% | 0.60% |
| NaOH | As needed | As needed |
| pH | 12.0 | 12.0 |

TABLE 4

Standard Biocide Formulations

| Reagents | 20 | 21 |
|---|---|---|
| Sodium Hypochlorite | 0.10% | — |
| N-alkyl dimethyl benzyl & ethylbenzyl ammonium chlorides | — | 0.10% |
| Tetra-Sodium Ethylenediaminetetraacetate | — | 0.02% |
| pH | 12.0 | 12.0 |

The concentrations are listed as percent active in the formulation.

These prototype formulations were evaluated for sanitizing efficacy versus model biofilms. The model biofilms were grown according to a method disclosed in U.S. provisional No. 60/138,354, incorporated by reference herein. This method was also subsequently published ("A Model Biofilm for Efficacy Assessment of Antimicrobials versus Biofilm Bacteria", Ursula K. Charaf, Shannon L. Bakich and Diane M. Falbo, in "Biofilms: The Good, The Bad and The Ugly." Contributions made at the Fourth Meeting of the Biofilm Club held at Gregynog Hall, Powys, 18–20 Sep. 1999, pp. 171–177). This method involves growing a biofilm on inoculated filter paper (Whatman qualitative #2) placed on top of 40 ml of Tryptic Soy Agar. The inoculum is prepared by first diluting a 24-hour culture of the desired biofilm forming organism 1/10 in phosphate-buffered saline solution. The filter paper is then inoculated with 1.0 ml of the diluted culture. Inoculum is pipetted onto the filter paper so that the entire paper surface is evenly moistened. Sterile glass coupons (slides) are aseptically placed on top of the inoculated filter paper and lightly pressed down. The biofilm is allowed to grow at room temperature. After approximately 24 hours, the biofilm is re-moistened with a 1/100 dilution of tryptic soy broth pipetted onto the exposed filter paper between the glass coupons. The slides are aseptically removed from the surface of the filter paper after 48±2 hours of growth. Each slide is placed on top of two pieces of filter paper, biofilm side-up, in a glass petri dish. The slides are then placed in a 35±2° C. incubator to dry for 30 minutes. Following this drying period, the biofilm-covered slides are ready to be treated.

Except where explicitly noted, a 5-minute contact time was employed for each treatment using 4–6 slides per treatment. The biofilm-covered slides were sprayed with the treatment until thoroughly wetted (approximately 3 sprays/slide; approximately 3 ml of product). Following the 5-minute contact time, the slides were placed in a sterile jar containing 10 ml of 2× Letheen Neutralizing broth. The treatment procedure used is a modification of the current U.S. EPA Non-Food Contact Sanitizer Test (DIS/TSS-10). Any remaining biofilm was then removed from the slides by scraping directly into the neutralizing broth. (This is the first dilution.) The samples were then homogenized for 1 minute at ½ maximal speed to disperse the cells. The cell suspensions were then serially diluted and plated on Tryptic Soy Agar. Cells surviving the treatment were counted as CFU's after 48 hours of incubation.

Efficacy was evaluated versus *Staphylococcus aureus* (ATCC No. 6538), *Enterobacter aerogenes* (ATCC No. 13048), and/or *Klebsiella pneumoniae* (ATCC No. 4352) biofilms. Parallel tests were run using a 0.01% solution of Triton X-100 (isooctylphenoxy-polyethoxyethanol with 9–10 mole oxyethylene) in an identical manner to serve as a control. The results for the test solutions were compared to the control and are reported as log reduction of the test organism versus the control counts. The log reductions were calculated according to the method described in "Calculating the Log Reduction and the Standard Error for Disinfection Studies—Formulas and Numerical Examples" (Hamilton, Martin A. and Heringstad, Becky E., Internal publication, Montana State University, Version 4, Sep. 24, 1998.). A "3.00 log reduction" means that 99.9% of the organisms have been killed. Three untreated slides were also scraped into the neutralizing broth and processed in the same way as the treated slides. These serve as a control to determine the total number of cells per slide ($10^8$ to $10^9$ cells per slide).

Results

TABLE 5

*K. pneumoniae*

| Formulation Code | Formulation pH | Log Reduction |
|---|---|---|
| Formula 1 | Acidic | 0.34 |
| Formula 2 | Acidic | 0.36 |
| Formula 3 | Acidic | 6.08 |
| Formula 4 | Acidic | 6.16 |
| Formula 5 | Acidic | 0.60 |

TABLE 5-continued

*K. pneumoniae*

| Formulation Code | Formulation pH | Log Reduction |
|---|---|---|
| Formula 6 | Acidic | 8.41 |
| Formula 7 | Acidic | 7.71 |
| Formula 8 | Acidic | 5.91 |
| Formula 9 | Acidic | 7.40 |
| Formula 10 | Acidic | 6.46 |
| Formula 15 | Neutral | 3.26 |
| Formula 16 | Neutral | 1.92 |
| Formula 17 | Neutral | 1.54 |
| Formula 18 | Alkaline | 0.73 |
| Formula 20 | Alkaline | 0.49 |
| Formula 21 | Alkaline | 1.60 |

TABLE 6

*S. aureus*

| Formulation Code | Formulation pH | Log Reduction |
|---|---|---|
| Formula 1 | Acidic | 1.92 |
| Formula 3 | Acidic | 6.12 |
| Formula 4 | Acidic | 5.18 |
| Formula 5 | Acidic | 4.98 |
| Formula 10 | Acidic | 6.61 |
| Formula 11 | Acidic | 3.97 |
| Formula 12 | Acidic | 4.06 |
| Formula 13 | Acidic | 4.12 |
| Formula 14 | Acidic | 6.05 |
| Formula 15 | Neutral | 3.01 |
| Formula 18 | Alkaline | 1.99 |
| Formula 19 | Alkaline | 1.99 |
| Formula 20 | Alkaline | 2.25 |
| Formula 21 | Alkaline | 2.96 |

TABLE 7

*E. aerogenes*

| Formulation Code | Formulation pH | Log Reduction |
|---|---|---|
| Formula 3 | Acidic | 6.31 |
| Formula 4 | Acidic | 5.96 |
| Formula 20 | Alkaline | 0.57 |

Acidic Compositions: Successful Combinations of Ingredients

Formulas 1 and 2 lack solvent and surfactant respectively. It becomes evident upon comparison of the log reductions achieved by these formulations to those achieved by formulations containing the combination of acid, surfactant and alcohol solvents (formulas 3, 4, 6, 7, 8, 9, and 10) that this latter combination is required to achieve good sanitizing efficacy against biofilm organisms. A log reduction of at least 4.0 (at a maximum 5-minute contact time) is desired to obtain good sanitizing performance, however, a log reduction of 4.5 or greater is preferred under the test conditions. It is also important to note that this combination is highly effective against biofilm organisms while conventional antimicrobial solutions such as quats or hypochlorite are largely ineffective (Formulas 20 and 21).

The nature of the solvent used is also critical to the formulation efficacy across a range of organisms. This is indicated by the results achieved by formula 5 which contained only 3.0% isopropanol solvent as opposed to the blend of glycol ethers used in the more efficacious formulations. While formula 5 was an effective biocidal composition against *Staphylococcus aureus* biofilm, biocidal performance against *Klebseilla pneumoniae* biofilm was poor. We believe the enhanced efficacy against a range of biofilm organisms may arise from the inclusion of a sparingly water-soluble solvent, such as ethylene glycol n-hexyl ether, in the solvent mixture.

Formulation pH is Important to Formula Efficacy

As the pH of the formula increases, the efficacy decreases sharply. With the exception of pH, the composition of formulas 3, 7, and 8 are similar to that of formulas 15 through 19. Comparing the results obtained for the acidic formulas (3, 7, and 8) to those obtained for the pH neutral and higher formulas (15–19), it is evident that the acidic formulations are more effective biofilm sanitizing compositions than the higher pH formulations. Therefore, the preferred compositions of this invention would have a pH of about 5 or below. The most preferred compositions would have a pH of about 4 or below. The role of formulation pH in achieving antimicrobial efficacy against biofilm organisms does not appear to be organism specific, as similar results are seen for *E. aerogenes*, *K. pneumoniae* (both gram-negative), and *S. aureus* (gram-positive) biofilms.

B. Comparison of the Composition of the Present Invention to other Cleaners

We tested a composition of the present invention, J-2975, against other cleaners to evaluate the relative efficacy of the present invention in log reduction of both gram-positive and gram-negative biofilms. Tables 8–12 below disclose the results of comparing various formulae with J-2975. The comparative test formulae were derived from U.S. Pat. Nos. 4,647,458; 5,962,388; 4,759,867 and 6,221,823 and evaluated using a 5 minute contact time as described above in paragraphs [0032]–[0036]. Where possible, the Tables indicate the example number taken from the relevant patent. In no case was log reduction at least log 4 for both gram-positive and gram-negative bacteria. In contrast, J-2975 reduced both gram-positive and gram-negative biofilm by at least log 6 using a 1 minute contact time.

Chemical Key

SLS=Sodium lauryl sulfate (Stepanol WAC, Stepan Company)
LAS=Sodium dodecylbenzene sulfonate (Biosoft D40, Stepan Company)
HLAS=Dodecylbenzene sulfonic acid (Biosoft S-100, Stepan Company)
PnP=Propylene glycol n-propyl ether
PnB=Propylene glycol n-butyl ether
DPnB=Dipropylene glycol n-butyl ether
Butyl carbitol=Diethylene glycol n-butyl ether
Hexyl carbitol=Diethylene glycol n-hexyl ether
SL-62=Plurafac SL-62 (BASF Corp.)
2A1=Dowfax 2A1 (Dow Chemical Company)
Bardac 22 (Lonza Corp.)
Preventol BP (Bayer Corp.)
BTC 888=BTC 888 (Stepan Company)

TABLE 8

U.S. Pat. No. 4,647,458 - Efficacy against biofilm evaluated using a 5 minute contact time.

| Log Reduction | | Formula Composition | | | | |
|---|---|---|---|---|---|---|
| S. aureus | K. pneumoniae | Ethanol | Lactic Acid | Acetic Acid | Phosphoric Acid | pH |
| 1.71 | 1.52 | 8.0 | 6.0 | 0.0 | 0.5 | 2.2 |
| 1.29 | 1.68 | 8.0 | 0.0 | 6.0 | 0.5 | 2.5 |

TABLE 9

U.S. Pat. No. 5,962,388 - Efficacy against biofilm evaluated using a 5 minute contact time.

| Log Reduction | | Formula Composition | | | | | | | | | |
|---|---|---|---|---|---|---|---|---|---|---|---|
| S. aureus | K. pneumoniae | Example | LAS | SLS | BTC 888 | DPnB | Citric Acid | Ammonia | Xanthan Gum | Polyvinyl pyrrolidone | Perfume | pH |
| 5.63 | 3.64 | 5 | 1.6 | 1.0 | 0.2 | 4.5 | 4.5 | To pH 3 | 0.01 | 0.0 | 0.2 | 3.3 |
| 5.42 | 3.10 | 6 | 1.6 | 1.0 | 0.2 | 4.0 | 4.5 | To pH 3 | 0.01 | 0.1 | 0.2 | 3.3 |
| 6.10 | 3.13 | 2 | 1.6 | 1.0 | 0.0 | 4.5 | 4.5 | To pH 3 | 0.01 | 0.0 | 0.2 | 3.3 |

TABLE 10

U.S. Pat. No. 4,759,867 - Efficacy against biofilm evaluated using a 5 minute contact time.

| Log Reduction | | Formula Composition | | | | | |
|---|---|---|---|---|---|---|---|
| S. aureus | K. pneumoniae | Example | HLAS | Ethanol | Xanthan Gum | Bardac 22 | Preventol BP | pH |
| 2.58 | 3.30 | 57 | 5.0 | 5.0 | 0.1 | 0.3 | 0.0 | 2.4 |
| 4.35 | 3.19 | 58 | 5.0 | 5.0 | 0.1 | 0.0 | 0.25 | 2.5 |

TABLE 11

U.S. Pat. No. 6,221,823 B1 - Efficacy against biofilm using a 5 minute contact time.

| Log Reduction | | Formula Composition | | | | | | | | | | |
|---|---|---|---|---|---|---|---|---|---|---|---|---|
| S. aureus | K. pneumoniae | Example | SL-62 | SLS | 2A1 | PnP | PnB | Citric Acid | Lactic Acid | Glycolic Acid | Xanthan Gum | Fragrance | pH |
| 5.82 | 3.21 | 8 | 1.00 | 3.00 | 3.00 | 0.90 | 3.90 | 2.50 | 3.57 | 0.20 | 0.00 | 0.20 | 3.0 |
| 3.94 | 2.34 | 15 | 1.00 | 3.00 | 3.00 | 0.90 | 3.90 | 2.50 | 0.00 | 3.57 | 0.60 | 0.20 | 3.0 |

TABLE 12

J2975 - Efficacy against bioflim evaluated using a 1 minute contact time.

| Log Reduction | | Formula Composition | | | | | |
|---|---|---|---|---|---|---|---|
| S. aureus | K. pneumoniae | Example | LAS | Lactic Acid | Butyl Carbitol | Hexyl Carbitol | pH |
| 6.35 | 7.42 | J-2975 | 6.75 | 5.0 | 3.0 | 2.0 | 2.2 |

INDUSTRIAL APPLICABILITY

The present invention provides fast-acting biocidal compositions that effectively kill biofilm-bound microorganisms on a plurality of contaminated surfaces. The compositions may be produced by commercially available liquid manufacturing techniques and equipment. In addition, the inventive solutions may be applied conveniently to a contaminated surface by mopping, spraying, wiping and the like. Further, standard dispensers such as a trigger sprayer and impregnated wipes may be utilized.

What is claimed is:

1. A method of substantially reducing the number of viable microorganisms within biofilm on a surface comprising the step of applying to the surface a composition comprising:
   (a) between 0.1% and 10% by weight of an anionic surfactant selected from the group consisting of alkyl sulfates, alkyl sulfonates, aryl sulfonates with alkyl or aryl substituents;
   (b) between 0.1% and 10% by weight of an acid, wherein the acid is selected from the group consisting of acids having a dissociation constant of about $1\times10^{-2}$ to about $1\times10^{-5}$ at 25° C.; and
   (c) between 0.5% and 10% by weight of a monohydric alcohol solvent selected from the group consisting of the following formulae:
   (I) R—O—$CH_2CH_2$—OH, where R is butyl, pentyl, hexyl, phenyl, or benzyl;
   (II) R—O—($CH_2CH_2$—O)$_2$H, where R is butyl, pentyl, hexyl, phenyl, or benzyl;
   (III) R'—O—$CH_2$CH—($CH_3$)OH, where R' is propyl, butyl, pentyl, hexyl, phenyl, or benzyl;
   (IV) R'—O($CH_2$CH—($CH_3$)O)$_2$H, where R' is methyl, ethyl, propyl, butyl, pentyl, hexyl, phenyl, or benzyl;
   (V) R"—OH, where R" is $C_nH_{2n+1}$, where n≧4, and
   (VII) R'"—OH, where R'"=benzyl, $C_6H_5$—$CH_2CH_2$,
   wherein the pH of the composition is between pH 1 and pH 5, and wherein the composition is applied to the surface and at least a log 4 reduction of viable gram negative and gram positive organisms occurs within 5 minutes.

2. The method of claim 1 wherein the anionic surfactant is selected from the group consisting of:
   (i) linear $C_8$ to $C_{16}$ alkyl sulfates;
   (ii) linear $C_8$ to $C_{16}$ alkyl sulfonates;
   (iii) $C_8$ to $C_{16}$ alkyl benzenesulfonates;
   (iv) $C_6$ to $C_{16}$ alkyl diphenyloxide disulfonates; and
   (v) $C_4$ to $C_{16}$ alkylated naphthalene sulfonates.

3. The method of claim 1 wherein the acid is selected from the group consisting of carboxylic acids having a dissociation constant of about $1\times10^{-2}$ to about $1\times10^{-5}$ at 25° C.

4. The method of claim 1 wherein the solvent is elected from the group consisting of:
   (I) R—O—$CH_2CH_2$—OH, where R is pentyl, hexyl, phenyl, or benzyl;
   (II) R—O—($CH_2CH_2$—O)2H, where R is pentyl, hexyl, phenyl, or benzyl;
   (III) R'—O—$CH_2$CH—($CH_3$)OH, where R' is butyl, or phenyl;
   (IV) R'—O($CH_2$CH—($CH_3$)O)$_2$H, where R' is butyl;
   (V) R"—OH, where R" is $C_nH_{2n+1}$, where n≧4, and
   (VII) R'"—OH, where R'"=benzyl, $C_6H_5$—$CH_2CH_2$.

5. The method of claim 1 wherein the anionic surfactant is present in an amount from about 0.25% to about 8% by weight of the composition.

6. The method of claim 1 wherein the anionic surfactant is present in an amount from about 0.5% to about 5% by weight of the composition.

7. The method of claim 2 wherein the anionic surfactant has an alkali metal or ammonium cation counterion of (i) to (v).

8. The method of claim 2 wherein the anionic surfactant is sodium lauryl sulfate or sodium dodecylbenzene sulfonate.

9. The method of claim 1 wherein the acid is selected from the group consisting of citric acid, lactic acid, glycolic acid, gluconic acid, glucoheptonic acid, malic acid, malonic acid, glutaric acid, succinic acid, adipic acid, formic acid, oxalic acid, acetic acid, propanoic acid, benzoic acid, phthalic acid, sorbic acid, fumaric acid, tartaric acid, and mixtures thereof.

10. The method of claim 1 wherein the acid is selected from the group consisting of low molecular weight poly (acrylic) acid, poly(maleic acid) homopolymers and copolymers, and mixtures thereof.

11. The method of claim 1 wherein the acid is present in an amount from about 0.25% to about 8.0% by weight of the composition.

12. The method of claim 1 wherein the acid is present in an amount from about 0.5% to about 5.0% by weight of the composition.

13. The method of claim 1 wherein the amount of solvent is in the range from about 1.0% to about 5% by weight of the composition.

14. The method of claim 1 wherein the solvent is elected from the group consisting of aliphatic alcohols and glycol ethers having a maximum solubility in water of about 20% by weight.

15. The method of claim 1 wherein the composition additionally comprises less than about 10% by weight of a low molecular weight alcohol selected from the group consisting of ethanol, n-propanol, iso-propanol, ethylene glycol mono-propyl ether, propylene glycol mono-ethyl ether, diethylene glycol mono-ethyl ether, and diethylene glycol mono-propyl ether.

16. The method of claim 14 wherein the glycol ether is selected from the formulae:

(I) R—O—$CH_2CH_2$—OH, where R is pentyl, hexyl, phenyl, or benzyl;

(II) R—O—($CH_2CH_2$—O)$_2$H, where R is pentyl, hexyl, phenyl, or benzyl;

(III) R'—O—$CH_2$CH—($CH_3$)OH, where R' is butyl, pentyl, hexyl phenyl, or benzyl; and (IV) R'—O($CH_2$CH—($CH_3$)O)$_2$H, where R' is butyl, pentyl, hexyl, phenyl, or benzyl;

and mixtures thereof.

17. The method of claim 1 wherein the solvent is selected from the group consisting of n-butanol, benzyl alcohol, 2-phenylethanol, ethylene glycol phenyl ether, ethylene glycol n-pentyl ether, ethylene glycol n-hexyl ether, ethylene glycol benzyl ether, propylene glycol phenyl ether, propylene glycol benzyl ether, propylene glycol n-butyl ether, diethylene glycol n-pentyl ether, diethylene glycol n-hexyl ether, and dipropylene glycol n-butyl ether.

18. The method of claim 1 wherein the solvent is a mixture selected from a first group consisting of at least one completely water-miscible aliphatic alcohol or glycol ether, in combination with a second group consisting of at least one aliphatic alcohol or glycol ether having a maximum solubility in water of about 20% by weight.

19. A method of substantially reducing the number of viable microorganisms within biofilm on a surface comprising the step of applying to the surface a composition comprising:

(a) between 0.1% and 10% by weight of an anionic surfactant selected from the group consisting of alkyl sulfates, alkyl sulfonates, and aryl sulfonates with alkyl or aryl substituents;

(b) between 0.1% and 10% by weight of an acid, wherein the acid is selected from the group consisting of acids having a dissociation constant of about $1\times10^{-2}$ to about $1\times10^{-5}$ at 25° C.; and (c) between 0.5% and 10% by weight of a monohydric alcohol solvent, wherein the alcohol is selected from the group consisting of th following formulae:

(I) R—O—$CH_2CH_2$—OH, where R is butyl, pentyl, hexyl, phenyl, or benzyl;

(II) R—O—($CH_2CH_2$—O)$_2$H, where R is butyl, pentyl, hexyl, phenyl, or benzyl;

(III) R'—O—$CH_2$CH—($CH_3$)OH, where R' is propyl, butyl, pentyl, hexyl, phenyl, or benzyl;

(IV) R'—O($CH_2$CH—($CH_3$)O)$_2$H, where R' is methyl, ethyl, propyl, butyl, pentyl, hexyl, phenyl, or benzyl, (V) R''—OH, where R'' is $C_nH_{2n+1}$, where $n \geq 4$, and (VII) R'''—OH, where R'''=benzyl, $C_6H_5$—$CH_2CH_2$, wherein the pH of the composition is between pH 1 and pH 5, and wherein the composition is applied to the surface and at least a log 4 reduction of viable gram negative and gram positive organisms occurs within 1 minute.

20. A method of substantially reducing the number of viable microorganisms within biofilm on a surface comprising the step of applying to the surface a composition comprising:

(a) between 0.1% and 10% by weight of an anionic surfactant selected from the group consisting of alkyl sulfates, alkyl sulfonates, and aryl sulfonates with alkyl or aryl substituents;

(b) between 0.1% and 10% by weight of an acid, wherein the acid is selected from the group consisting of acids having a dissociation constant of about $1\times10^{-2}$ to about $1\times10^{-5}$ at 25° C.; and (c) between 0.5% and 10% by weight of a monohydric alcohol solvent, wherein the alcohol is selected from the group consisting of th following formulae:

(I) R—O—($CH_2CH_2$—OH, where R is butyl, pentyl, hexyl, phenyl, or benzyl;

(II) R—O—($CH_2CH_2$—O)$_2$H, where R, is butyl, pentyl, hexyl, phenyl, or benzyl;

(III) R'—O—$CH_2$CH—($CH_3$)OH, where R' is propyl, butyl, pentyl, hexyl, phenyl, or benzyl;

(IV) R'—O($CH_2$CH—($CH_3$)O)$_2$H, where R' is methyl, ethyl, propyl, butyl, pentyl, hexyl, phenyl, or benzyl, (V) R''—OH, where R'' is $C_nH_{2n+1}$, where $n \geq 4$, and (VII) R'''—OH, where R'''=benzyl, $C_6H_5$—$CH_2CH_2$, wherein the pH of the composition is between pH 1 and pH 5, and wherein the composition is applied to the surface and at least a log 5 reduction of viable gram negative and gram positive organisms occurs within 5 minutes.

21. A method of substantially reducing the number of viable microorganisms within biofilm on a surface comprising the step of applying to the surface a composition comprising:

(a) between 0.1% and 10% by weight of an anionic surfactant selected from the group consisting of alkyl sulfates, alkyl sulfonates, aryl sulfonates with alkyl or aryl substituents;

(b) between 0.1% and 10% by weight of an acid, wherein the acid is lactic acid; and (c) between 0.5% and 10% by weight of a monohydric alcohol solvent, wherein the alcohol is selected from the group consisting of the following formulae:

(I) R—O—$CH_2CH_2$—OH, where R is butyl, pentyl, hexyl, phenyl, or benzyl;

(II) R—O—($CH_2CH_2$—O)$_2$H, where R is butyl, pentyl, hexyl, phenyl, or benzyl;

(III) R'—O—$CH_2$CH—($CH_3$)OH, where R' is propyl, butyl, pentyl, hexyl, phenyl, or benzyl;

(IV) R'—O($CH_2$CH—($CH_3$)O)$_2$H, where R' is methyl, ethyl, propyl, butyl, pentyl, hexyl, phenyl, or benzyl, (V) R''—OH, where R'' is $C_nH_{2n+1}$, where $n \geq 4$, and (VII) R'''—OH, where R'''=benzyl, $C_6H_5$—$CH_2CH_2$, wherein the pH of the composition is between pH 1 and pH 5, and wherein the composition is applied to the surface and at least a log 4 reduction of viable gram negative and gram positive organisms occurs within 5 minutes.

* * * * *